United States Patent [19]
Eizenhöfer

[11] Patent Number: 6,146,340
[45] Date of Patent: Nov. 14, 2000

[54] ELECTROMAGNETIC SHOCK WAVE SOURCE HAVING A MECHANICALLY PRESTRESSED ELECTRICALLY CONDUCTIVE MEMBRANE

[75] Inventor: Harald Eizenhöfer, Seefeld, Germany

[73] Assignee: Dornier Medizintechnik GmbH, Germany

[21] Appl. No.: 08/824,964

[22] Filed: Mar. 27, 1997

[30] Foreign Application Priority Data

Mar. 27, 1996 [DE] Germany .......................... 196 12 061

[51] Int. Cl.⁷ .................................................. A61B 17/22
[52] U.S. Cl. ................................................. 601/4; 606/127
[58] Field of Search ............................ 601/4, 2; 606/127

[56] References Cited

FOREIGN PATENT DOCUMENTS

| | | |
|---|---|---|
| 37 42 500 A1 | 12/1987 | Germany . |
| 41 18 306 A1 | 6/1991 | Germany . |
| 41 30 796 A1 | 9/1991 | Germany . |
| 42 42 131 C1 | 12/1992 | Germany . |
| 196 12 061 C1 | 3/1996 | Germany . |

*Primary Examiner*—Marvin M. Lateef
*Assistant Examiner*—Eleni Mantis Mercader
*Attorney, Agent, or Firm*—Evenson, McKeown, Edwards & Lenahan, P.L.L.C.

[57] ABSTRACT

The shock wave source according to the invention has a membrane of an electrically conductive material which is connected on one side with a propagation medium and, on the other side, with a flat coil. The membrane is subjected to a mechanical prestress which acts radially on it by virtue of the clamping of its edge area by at least one member which has a projection which extends in a direction normal to the plane of the membrane.

8 Claims, 1 Drawing Sheet

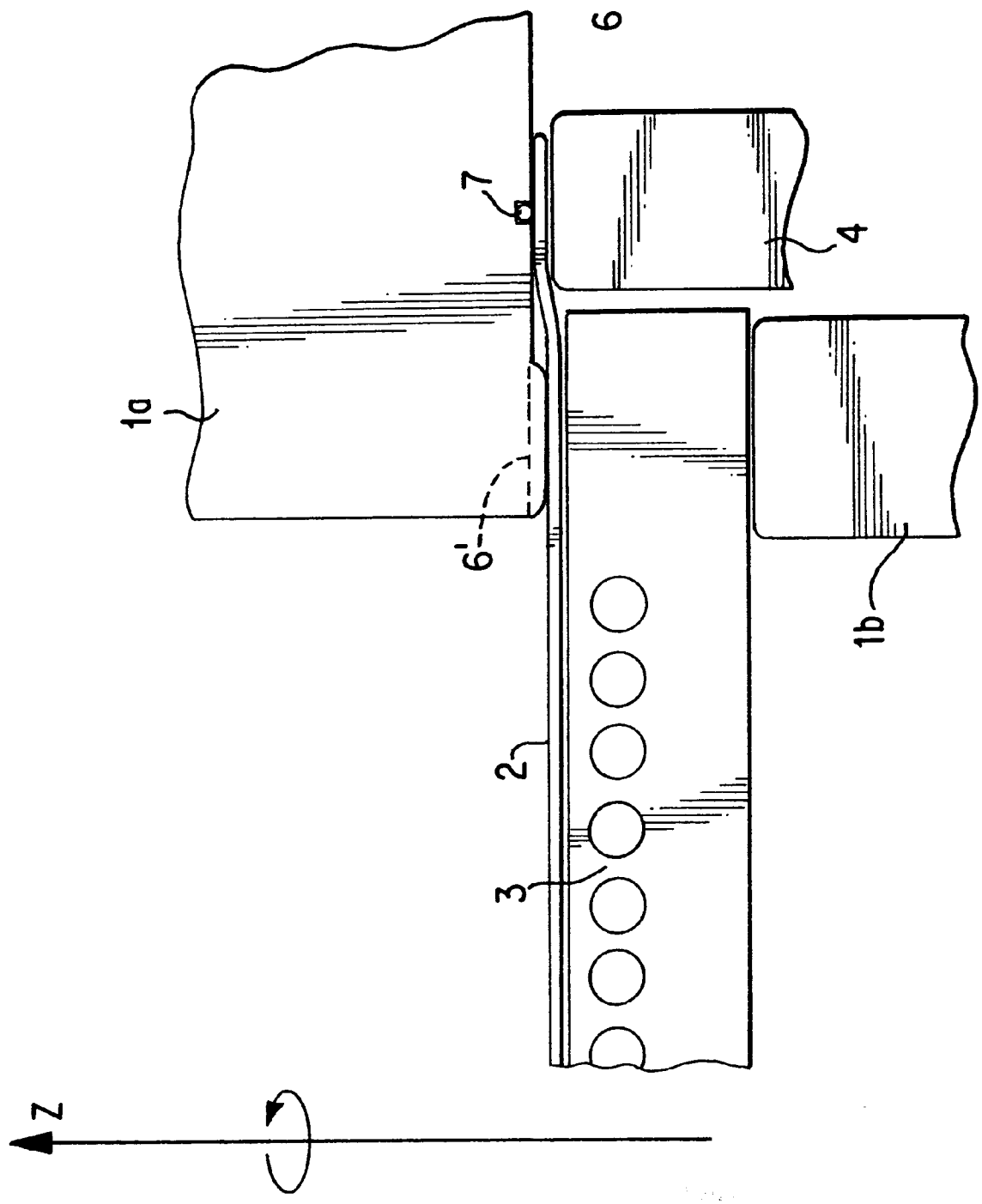

ELECTROMAGNETIC SHOCK WAVE SOURCE HAVING A MECHANICALLY PRESTRESSED ELECTRICALLY CONDUCTIVE MEMBRANE

This application claims the priority of German priority document 196 12 061.6, the disclosure of which is expressly incorporated by reference herein.

BACKGROUND AND SUMMARY OF THE INVENTION

The present invention relates to an electromagnetic shock wave source in which the apparatus for generating the shock waves has a mechanically prestressed membrane made of an electrically conductive material, one side of which contacts an acoustic propagation medium, and the other side of which, is connected by way of an insulator with a flat coil.

Such shock wave sources are used for many different purposes. For example, in the medical field they are used for non-invasive crushing of concrements situated in a patient's body and non-invasive treatment of pathological tissue changes. In the former case, positive pressure pulses—that is, excess pressure pulses—are used. In addition, such shock wave sources can be used, for example, to test materials in order to act upon them by pressure pulses.

In such devices, the shock wave source is appropriately acoustically coupled with the object which is to be exposed to sonic waves, so that the pressure pulses generated in the acoustic propagation medium can be introduced therein. An important component of such a shock wave source is the part which generates the shock waves, which normally consists of an electrically conductive membrane and a flat coil situated opposite it. The shock waves are generated by connecting the flat coil to a high-voltage supply—for example, a capacitor which is charged to several kV. The discharge current flows through the flat coil, rapidly building up a magnetic field. The magnetic field, in turn, generates a current in the membrane, which is opposite to that of the flat coil, so that an opposing magnetic field is built up which moves the membrane abruptly away from the flat coil. The resulting shock wave is supplied to its intended destination (for example, a patient's body) via a corresponding acoustic propagation medium, such as degassed water.

In order to achieve a high efficiency (that is, the conversion of as much of the consumed electric energy as possible into acoustic shock wave energy), the membrane must rest against the flat coil as closely as possible, and must return to its starting position during the time period between two successive shock waves.

In conventional electromagnetic shock wave sources, it is therefore customary to evacuate the space between the coil and the membrane. To improve the electromagnetic coupling of the membrane with the coil, it is also customary as an alternative to apply an excess pressure to the propagation medium between the membrane and the patient, so that the membrane is pressed against the flat coil.

However, such a construction has certain disadvantages. Thus, particularly when no additional separating membrane is used, the excess pressure in the propagation medium can be used only in a low pressure range because the propagation medium (normally water in the case of all modern shock wave sources) is enclosed in a rubber-type double cushion which, in turn, can accommodate only a low excess pressure. In addition, to form and maintain the vacuum between the flat coil and the membrane, a vacuum pump and additional sealing measures are required. The excess pressure as well as the vacuum must be electrically controlled and monitored, which adds considerable servicing expenditures for the pumps generating the pressures.

German Patent Document DE C 4242131 describes an acoustic pressure pulse generator for generating acoustic pressure pulses in an acoustic propagation medium. The generator has a membrane that can be driven in a shock-like manner, adjoins the acoustic propagation medium and is mechanically prestressed so that it returns to its starting position after generating a pressure pulse. Before mounting, the membrane is curved toward the coil and is prestressed by pressing it along its edge against the shock exciting system, so that within its edge, the membrane rests against the shock exciting system, and is therefore subjected to compressive stress.

In this known pressure pulse generator, it must be ensured that, before a pressure pulse is generated, the membrane rests on the shock exciting system and, after a pressure pulse is generated, the membrane returns into its starting position. The membrane itself is a composite component consisting of a curved metallic disk which is mechanically connected (for example, by means of vulcanizing) to an edge part that can be clamped in place. In addition to the substantial technical expenditures required to manufacture such a composite component, there is also the significant disadvantage that a curved metallic disk can be placed flatly against the surface of a flat coil only by means of upsetting, axially acting forces without forming folds.

It is an object of the present invention to provide a shock wave source which has a particularly simple construction with a high efficiency at reasonable cost.

This object is achieved by the electromagnetic shock wave source according to the invention in which the electrically conductive membrane has a planar contour, and is prestressed by means of two structural parts which clamp the edge of the membrane and generate a force which acts in parallel to the surface of the membrane. One structural part has a recess into which the other structural part engages, while taking along the edge of the membrane.

The shock wave source according to the invention offers the advantages not only that the use of excess pressure in front of the membrane and/or of a vacuum between the membrane and the flat coil is unnecessary (thus eliminating all related expenditures for adjusting and monitoring the pressure, as well as for sealing), but also that a particularly simple construction is provided for the membrane and the flat coil generating the shock waves. The flat membrane requires no separate edge part to which it would have to be glued, so that the manufacturing is clearly less expensive.

Other objects, advantages and novel features of the present invention will become apparent from the following detailed description of the invention when considered in conjunction with the accompanying drawings.

BRIEF DESCRIPTION OF THE DRAWINGS

The single FIGURE is a sectional view of an edge part of a clamping-in of the membrane with the pertaining flat coil.

DETAILED DESCRIPTION OF THE DRAWINGS

In the FIGURE, reference number 1*a* and 1*b* designate structural parts of a shock wave source, which are used to clamp the peripheral edge of the part that generates the shock waves. The latter consists of a membrane 2 made of an electrically conductive material, one side of which is in contact with an acoustic propagation medium (not shown)

and the other side of which, by way of an insulator, is connected with a flat coil 3. The flat coil 3 can consist of helically arranged windings embedded in a corresponding insulator. As an additional insulator, a foil (not shown) can be arranged between the flat coil 3 and the membrane 2.

According to the invention, the metallic membrane 2 is subjected to a radial prestress generated by clamping the peripheral edge area of the generally circular membrane 2 between the structural parts 1*a* and 4. For this purpose, the bottom side 6 of the structural part 1*a* is provided with a shallow projection 6', and the surface of the structural part 4 which rests against the structural part 1*a* is designed so that, when the two structural parts 1*a,* 4 are fitted on one another (for example, by an axial screwing-together), the membrane 2 is pulled radially to the outside (in a manner similar to the known deep-drawing process). That is, the structural part 4 pulls the edge area of the membrane 2 over the shallow projection 6' and thereby deforms it. Reference number 7 indicates a seal between the structural part 1*a* and the surface of the membrane 2.

This radial clamping of the metallic membrane 2, which rests flatly against the flat coil 3, offers the important advantage that it ensures a durable plane contact of the membrane 2 on the flat coil 3. The membrane 2, which has a layer thickness of approximately 0.1 to 0.3 mm, may consist of aluminum alloys whose tensile strength is higher than 250 N/mm$^2$. A suitable material, for example, is an alloy of aluminum which has 1 to 4% manganese and/or magnesium and/or chromium.

According to the invention, it is important that the membrane which generates the shock waves rests as closely as possible against the flat coil between individual actuations thereof. The membrane is thus not only constructed to be plane but is also subjected to a radial prestress which prevents any bulging, except during the generating of the shock waves.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Electromagnetic shock wave source having a prestressed membrane made of an electrically conductive material, one side of which contacts an acoustic propagation medium, and the other side of which is connected by way of an insulator with a flat coil, wherein:

the membrane has a planar construction; and the membrane is prestressed in a direction parallel to a surface thereof, by an arrangement acting in parallel to the plane of the membrane.

2. Shock wave source according to claim 1 wherein:

the arrangement which prestresses the membrane comprises two structural parts which clamp the edge of the membrane; and one of said structural parts has a recess into which the other structural part engages, whereby the edge of the membrane is drawn radially outward.

3. Shock wave source according to claim 2 wherein the membrane comprises an alloy whose tensile strength is higher than 250 N/mm$^2$.

4. Shock wave source according to claim 3 wherein the alloy comprises aluminum with 1 to 4% of a material selected from the group consisting of at least one of manganese, magnesium and chromium.

5. Shock wave source according to claim 1 wherein the membrane comprises an alloy whose tensile strength is higher than 250 N/mm$^2$.

6. Shock wave source according to claim 5 wherein the alloy comprises aluminum with 1 to 4% of a material selected from the group consisting of at least one of manganese, magnesium and chromium.

7. An electromagnetic shock wave generator comprising a substantially planar membrane made of an electrically conductive material;

a substantially planar electric coil arranged in close parallel proximity to said membrane; and first and second clamping members for clamping a peripheral edge portion of said membrane, at least one of said clamping members having a projection which extends perpendicular to said membrane, whereby said membrane is stressed radially outwardly when said edge portion is clamped.

8. Electromagnetic shock wave source having a prestretched membrane made of an electrically conductive material, one side of which contacts an acoustic propagation medium, and the other side of which is connected by way of an insulator with a flat coil, wherein:

the membrane has a planar construction; and the membrane is prestretched in a direction parallel to a surface thereof, by an arrangement acting in parallel to the plane of the membrane.

* * * * *